(12) United States Patent
Blaskowski et al.

(10) Patent No.: US 9,173,642 B2
(45) Date of Patent: Nov. 3, 2015

(54) ELONGATE MEDICAL DEVICE HANDLE AUTOLOCK

(71) Applicant: St. Jude Medical, Atrial Fibrillation Division, Inc., St. Paul, MN (US)

(72) Inventors: Stacie Marie Blaskowski, St. Louis Park, MN (US); Steven Andreas Anderson, Shakopee, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 246 days.

(21) Appl. No.: 13/765,128

(22) Filed: Feb. 12, 2013

(65) Prior Publication Data

US 2014/0228820 A1     Aug. 14, 2014

(51) Int. Cl.
| | |
|---|---|
| *A61B 17/00* | (2006.01) |
| *A61M 25/01* | (2006.01) |
| *A61B 18/14* | (2006.01) |
| *A61N 7/02* | (2006.01) |
| *A61B 18/00* | (2006.01) |
| *A61B 18/02* | (2006.01) |

(52) U.S. Cl.
CPC .......... *A61B 17/00* (2013.01); *A61M 25/0136* (2013.01); *A61B 18/1492* (2013.01); *A61B 2018/0091* (2013.01); *A61B 2018/0212* (2013.01); *A61N 7/022* (2013.01)

(58) Field of Classification Search
CPC .............. A61B 17/00; A61B 18/1492; A61B 2018/0091; A61B 2018/0212; A61M 25/0136; A61N 7/022
USPC .................. 600/374, 462, 564; 604/284, 199, 604/95.05; 606/41; 607/116; 439/669; 227/176.1; 411/374; 285/27
See application file for complete search history.

(56) References Cited

U.S. PATENT DOCUMENTS

| | | | | | |
|---|---|---|---|---|---|
| 4,139,222 | A | * | 2/1979 | Loland | 285/27 |
| 4,960,134 | A | * | 10/1990 | Webster, Jr. | 607/116 |
| 5,104,274 | A | * | 4/1992 | Omori | 411/374 |
| 5,441,483 | A | * | 8/1995 | Avitall | 604/95.05 |
| 6,332,633 | B1 | | 12/2001 | Fitoussi et al. | |
| 6,464,645 | B1 | * | 10/2002 | Park et al. | 600/462 |
| 6,743,227 | B2 | * | 6/2004 | Seraj et al. | 606/41 |
| 7,819,297 | B2 | * | 10/2010 | Doll et al. | 227/176.1 |
| 7,892,215 | B2 | * | 2/2011 | Melsheimer et al. | 604/284 |

(Continued)

FOREIGN PATENT DOCUMENTS

WO     94/04220     3/1994

OTHER PUBLICATIONS

International Search Report and Written Opinion in PCT Application No. PCT/US2014/015247 (Jun. 17, 2014).

*Primary Examiner* — William Thomson
*Assistant Examiner* — Victor Shapiro
(74) *Attorney, Agent, or Firm* — Dykema Gossett PLLC

(57) ABSTRACT

An embodiment of a handle assembly for an elongate medical device that may reduce the weight and/or expense of traditional handle may include an exterior adjusting knob extending along a longitudinal axis and configured to rotate about the axis, an insert, and a dowel pin. The insert may be configured to engage the adjusting knob and to rotate about the axis responsive to rotation of the adjusting knob. The insert may comprise an annular groove configured to engage a dowel pin, the annular groove comprising a sidewall comprising a chamfer. The dowel pin may be configured to engage the annular groove to resist rotation of the insert. In an embodiment, the insert may comprise plastic or polymer.

19 Claims, 9 Drawing Sheets

FIG.14B

(56) References Cited

U.S. PATENT DOCUMENTS

| | | | |
|---|---|---|---|
| 8,167,660 B2* | 5/2012 | Dilmaghanian et al. | 439/669 |
| 8,328,767 B2* | 12/2012 | Solomon et al. | 604/199 |
| 8,366,635 B2* | 2/2013 | Parihar et al. | 600/564 |
| 2005/0096590 A1 | 5/2005 | Gullickson et al. | |
| 2008/0009928 A1* | 1/2008 | Osypka et al. | 607/116 |
| 2010/0292784 A1 | 11/2010 | Giannetti et al. | |
| 2011/0264074 A1 | 10/2011 | Tegg et al. | |
| 2011/0282176 A1 | 11/2011 | Tegg | |

* cited by examiner

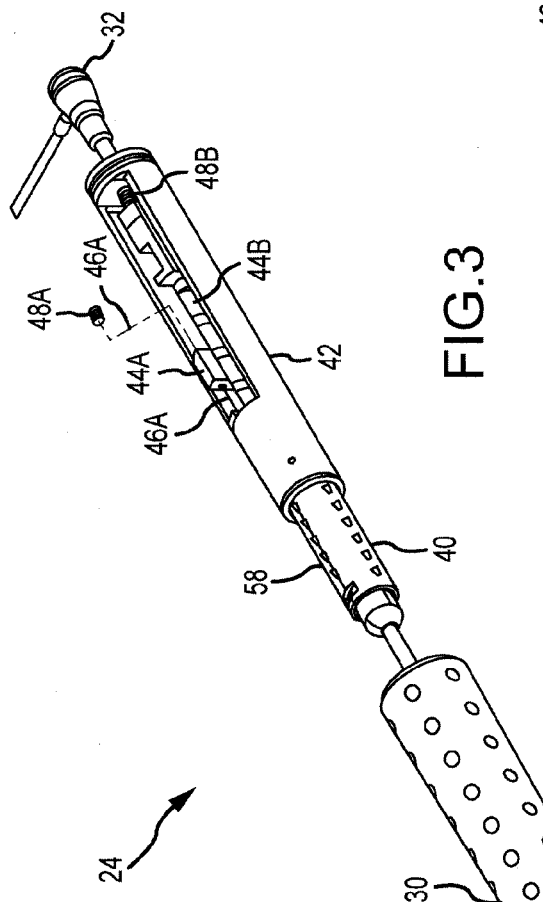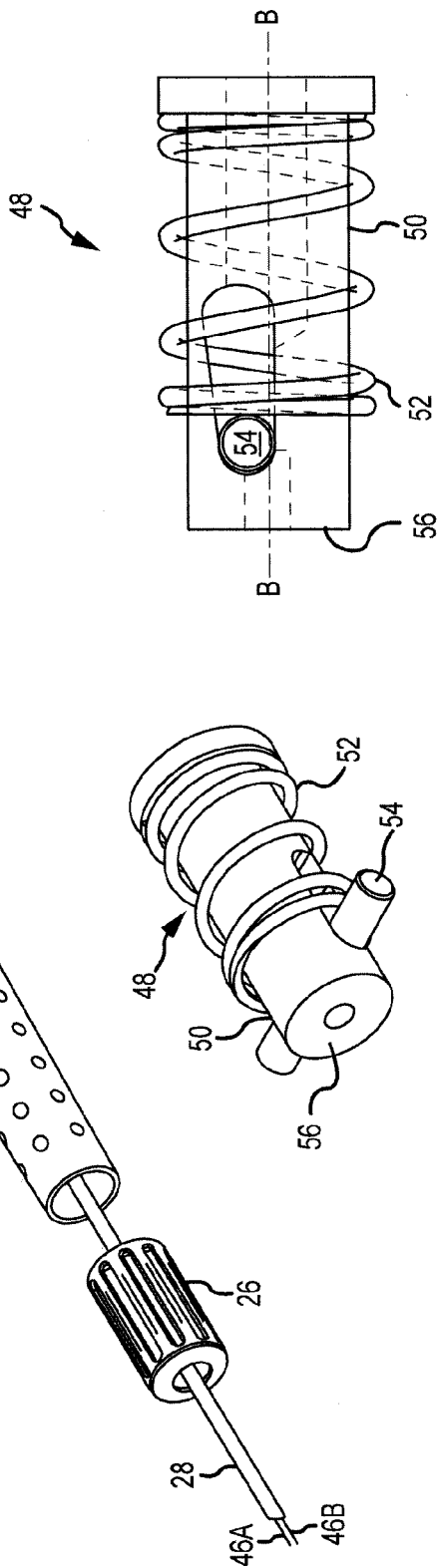

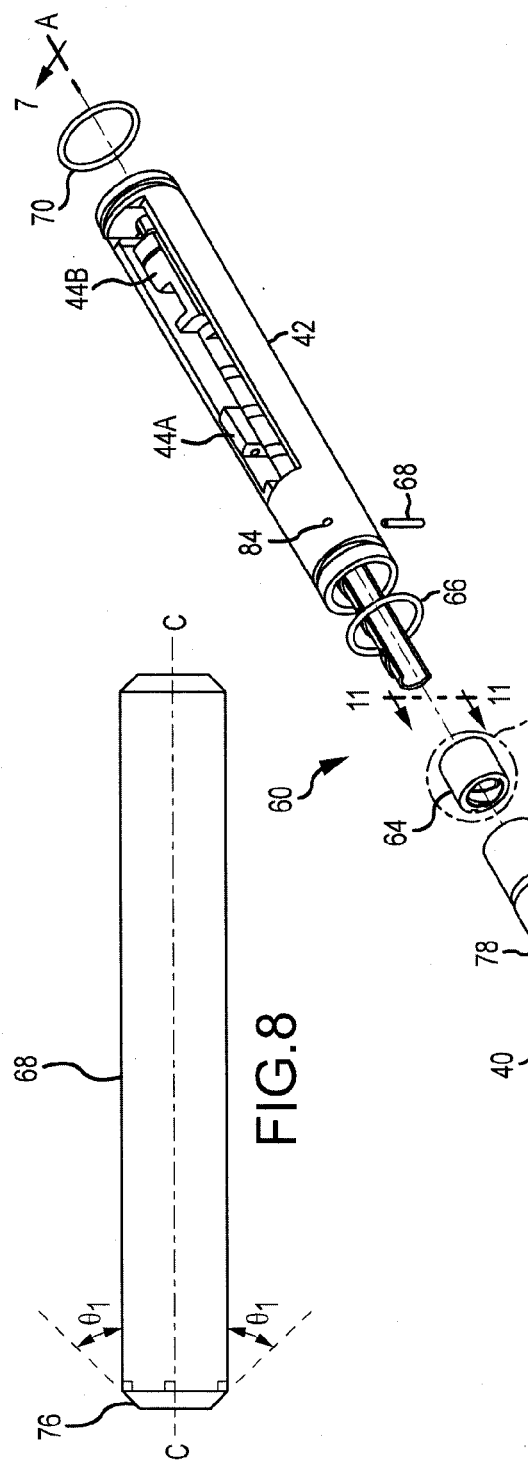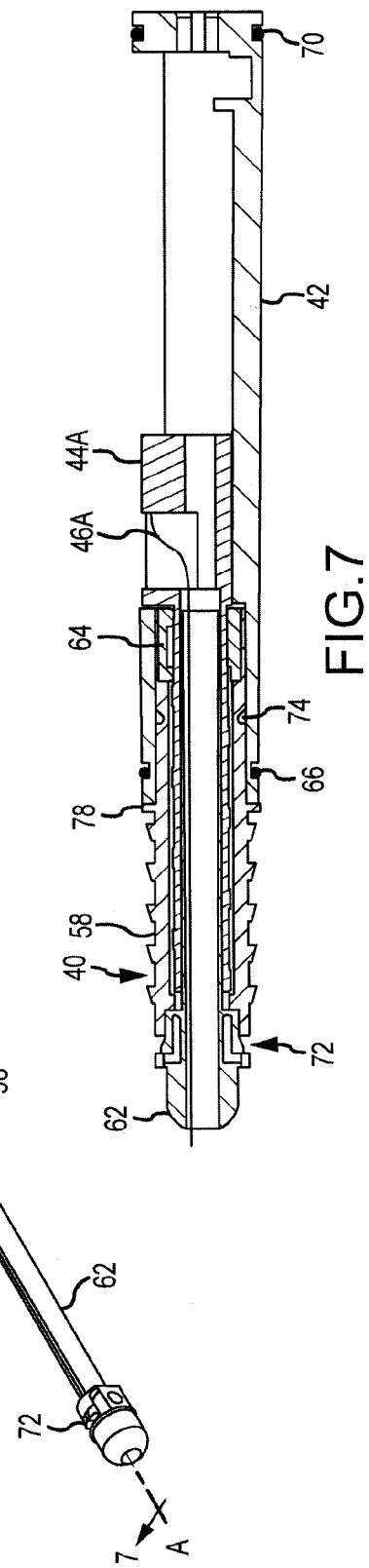

ELONGATE MEDICAL DEVICE HANDLE AUTOLOCK

BACKGROUND a. Technical Field

The instant disclosure relates to handle assemblies for elongate medical devices, including interior components of a handle assembly for resisting deflection of the shaft of the medical device.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like. Often, another medical device, called an introducer or sheath, is used to position a catheter within the heart.

To increase the ability to move and navigate an introducer or catheter within a patient's body, steerable introducers and catheters have been designed. Such steerable devices often have a steering mechanism near the distal end of the device. This steering mechanism typically includes a pull ring and one or more pull wires (or deflection wires) attached thereto and extending proximally towards an actuator that can place the wire or wires in tension. Placing a pull wire in tension may cause the distal end of the device to deflect in at least one plane. In this fashion, the introducer and/or catheter can be navigated through the tortuous path of a patient's vasculature to a target site.

The foregoing discussion is intended only to illustrate the present field and should not be taken as a disavowal of claim scope.

BRIEF SUMMARY

An embodiment of a handle assembly for a catheter that may reduce the weight and/or expense of a traditional catheter handle may include an exterior adjusting knob extending along a longitudinal axis and configured to rotate about the axis, an insert, and a dowel pin. The insert may be configured to engage the adjusting knob and to rotate about the axis responsive to rotation of the adjusting knob. The insert may comprise an annular groove configured to engage a dowel pin, the annular groove comprising a sidewall comprising a chamfer. The dowel pin may be configured to engage the annular groove to resist rotation of the insert. In an embodiment, the insert may comprise plastic or polymer.

Another embodiment of a handle assembly may include an exterior adjusting knob extending along a longitudinal axis and configured to rotate about the axis, a polymer or plastic insert, and a dowel pin. The insert may be configured to engage the adjusting knob and to rotate about the axis responsive to rotation of the adjusting knob. The insert may comprise an annular groove configured to engage a dowel pin. The dowel pin may be configured to engage the annular groove to resist rotation of the insert when no external force is applied to the adjusting knob, wherein the insert is configured to rotate relative to the dowel pin when an external force is applied to the adjusting knob.

An embodiment of an elongate medical device may comprise a shaft and a handle assembly. The shaft may comprise a distal end portion, a proximal end portion, a longitudinal axis extending through the distal and proximal end portions, and a pull wire coupled to the distal end portion configured to deflect the distal end portion. The handle assembly may be coupled to the proximal end portion of the shaft and may comprise an exterior adjusting knob extending along the axis and configured to rotate about the axis, an insert, and a dowel pin. The insert may be configured to engage the adjusting knob and to rotate about the axis responsive to rotation of the adjusting knob. The insert may comprise an annular groove configured to engage a dowel pin. The annular groove may comprise a sidewall, wherein rotation of the insert applies a tensile force to the pull wire to deflect the shaft distal end portion. The dowel pin may be configured to engage the annular groove to resist rotation of the insert. The shaft and handle assembly may be configured to allow another medical device to be passed therethrough.

BRIEF DESCRIPTION OF THE DRAWINGS

FIG. 3 is an exploded isometric view of an embodiment of the handle assembly of the elongate medical device of FIG. 2.

FIG. 4 is an enlarged isometric view of an embodiment of a clip subassembly of the handle assembly of FIG. 3.

FIG. 5 is a side view of the clip subassembly of FIG. 4.

FIG. 6 is an exploded isometric view of an embodiment of the interior assembly of the handle assembly of FIG. 3.

FIG. 7 is a cross-sectional view of the interior assembly illustrated in FIG. 6.

FIG. 8 is an enlarged side view of an embodiment of a dowel pin of the interior assembly of FIG. 6.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
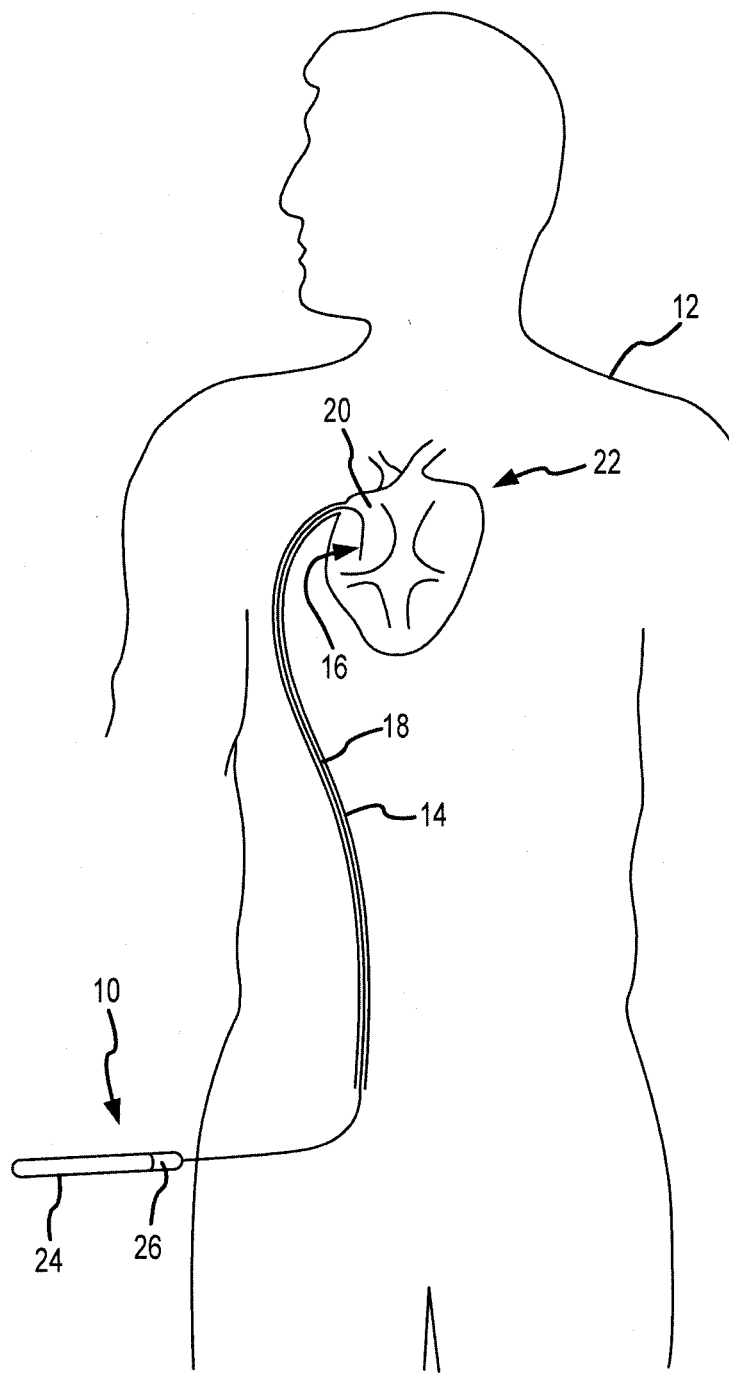
FIG. 1 is a diagrammatic view of an embodiment of an elongate medical device disposed in the body of a patient.

Referring now to the Figures, in which like reference numerals refer to the same or similar features in the various views, FIG. 1 is a diagrammatic view of an elongate medical device 10 disposed within a patient 12. More specifically, the elongate medical device 10 is disposed in the vasculature 14 of the patient 12, with a distal end portion 16 of a shaft 18 of the elongate medical device 10 disposed in a chamber 20 of the heart 22 of the patient 12. The elongate medical device 10 may also include a handle assembly 24 with an adjustment knob 26 for guiding the shaft 18 and deflecting the distal end portion 16 of the shaft 18.

The elongate medical device 10 may comprise, for example, a diagnostic and/or therapy delivery catheter, an introducer or sheath, or other like devices. For purposes of illustration and clarity, the description below will be with respect to an embodiment wherein the elongate medical device 10 comprises an introducer (i.e., introducer 10). It will be appreciated, however, that embodiments wherein the elongate medical device comprises devices other than an introducer remain within the spirit and scope of the present disclosure.

Figure 2:
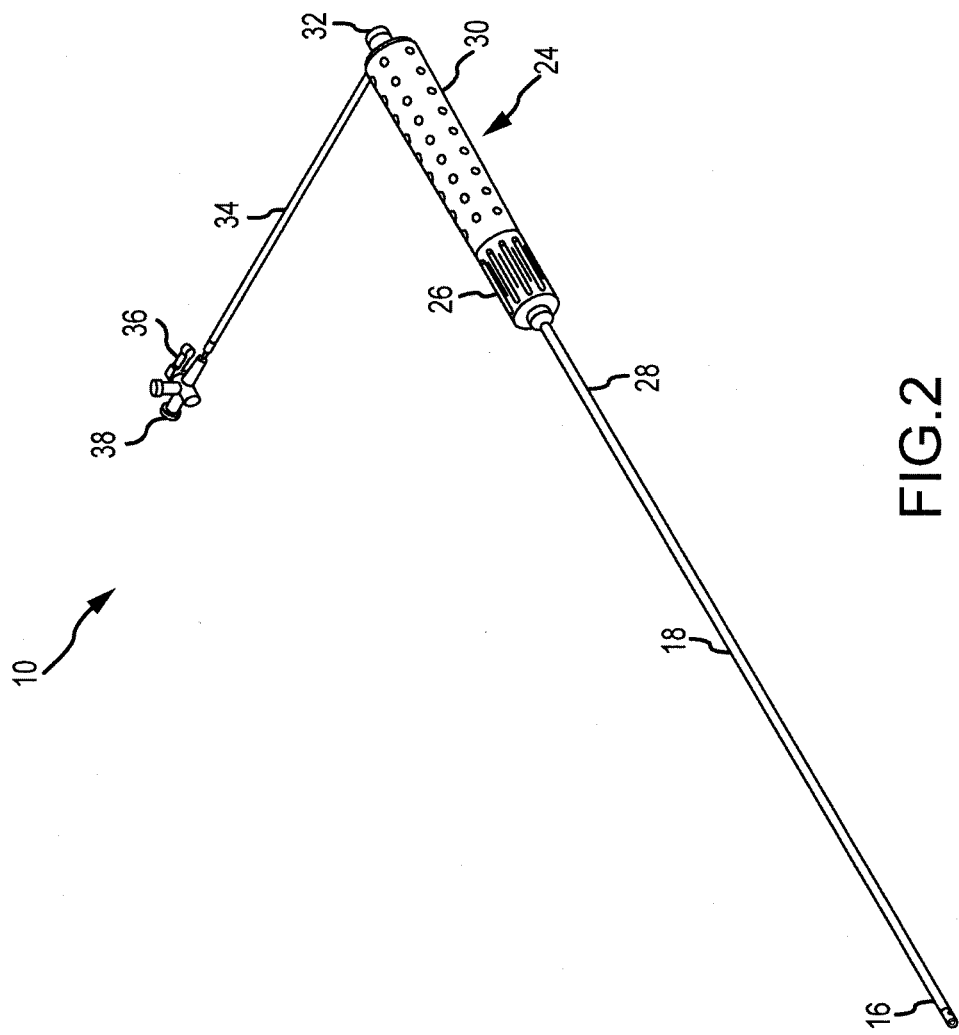
FIG. 2 is an isometric view of an embodiment of an elongate medical device.

Referring to FIGS. 1 and 2, in an exemplary embodiment, the introducer 10 may be configured to be inserted into the body of the patient 12, and more particularly, into the heart 22. The introducer 10 may include a shaft 18 having a proximal end portion 28 and a distal end portion 16, a handle assembly 24 including an adjustment knob 26 and a grip portion 30, a hemostasis valve 32, and an exterior fluid lumen 34 terminating in a stopcock 36, which may also include a luer lock connector 38 for connection to an irrigation system (not shown). The introducer 10 may further include other conventional components such as, for example and without limitation, one or more position sensors, a temperature sensor, additional sensors or electrodes, ablation elements (e.g., ablation tip electrodes for delivering RF ablative energy, high intensity focused ultrasound ablation elements, etc.), and corresponding conductors or leads. Additionally, the shaft may include one or more fluid lumens extending from the distal end portion 16 to the proximal end portion 28 (and, in an embodiment, into and though the handle assembly 24 for fluid coupling with the exterior fluid lumen 34) for the delivery and/or removal of one or more fluids such as, for example only, irrigation fluids, bodily fluids, and cryogenic ablation fluids.

The shaft 18 may also include one or more pull wires for deflecting a portion of the shaft such as, for example only and not by limitation, the distal end portion 16. Each pull wire may extend through the shaft 18 and be coupled with a pull ring within the shaft 18 or may otherwise be directly or indirectly attached to a portion of the shaft 18 where deflection is desired. Each pull wire may extend through the shaft 18 to the handle assembly 24.

The handle assembly 24 is provided to enable a clinician to guide the distal end portion 16 of the shaft 18 to a target site, such as a location within the chamber 20, to allow another medical device to be passed through the introducer 10 to perform a particular diagnostic and/or therapeutic function. Accordingly, the handle assembly 24 may be coupled with the proximal end portion 28 of the shaft 18 and may comprise an adjustment knob 26 and a grip portion 30. The grip portion 30 may be configured in size, shape, and materials to be comfortably and securely gripped by a clinician guiding the introducer 10. The adjustment knob 26 may be provided as an exterior mechanism through which a clinician can deflect the shaft 18 such as, for example, the distal end portion 16 of the shaft 18. The adjustment knob 26 may thus be coupled, directly or indirectly, with one or more pull wires 46A, 46B that extend through the shaft 18 as shown in FIG. 3.

Although embodiments of the handle assembly 24 are described herein with reference to a single adjustment knob 26 for deflecting the shaft 18, it should be understood that this disclosure is not so limited. Rather, alternative and/or additional known exterior mechanisms for applying a force to a pull wire or other control element are within the spirit and scope of this disclosure. For example, a single or multiple adjustment knobs may be provided, substantially as described in U.S. patent application publication no. 2011/0282176A1, which is hereby incorporated by reference in its entirety as though fully set forth herein.

FIG. 3 is an exploded isometric view of an embodiment of the handle assembly 24. In addition to the exterior adjustment knob 26 and grip portion 30, the handle assembly may comprise a number of interior components, such as an adjustment knob insert 40, a mounting shaft 42, and two slider blocks 44A, 44B. Each slider block 44A, 44B may be coupled, directly or indirectly, to a respective pull wire 46A, 46B. In an embodiment, each pull wire 46A, 46B may extend through a respective slider block 44A, 44B to a respective clip subassembly 48A, 48B disposed proximal of the slider block 44A, 44B. Each slider block 44A, 44B may be configured to move distally and proximally within the mounting shaft 42 to apply and release force to/from the respective clip subassembly 48A, 48B, which may correspondingly apply and release tensile forces to/from the pull wires 46. The adjustment knob insert 40 may be provided for transferring force from the adjustment knob 26 to the slider blocks 44A, 44B, and thus to actuate the pull wires 46 and deflect the shaft 18 (see FIGS. 1 and 2). Accordingly, the insert 40 may comprise a knob coupling portion 50 to secure the adjustment knob insert 40 to the adjustment knob 26 so that the two components rotate substantially in unison.

FIGS. 4 and 5 are, respectively, an enlarged isometric view and an enlarged side view of an embodiment of the clip subassembly 48, which may be employed as one or both of the clip subassemblies 48A and 48B, referenced above. The clip subassembly 48 may include a body 50 and a spring 52 disposed about an axis B and a pin 54. The body 50 may have a distal end surface 56 configured for contact with a slider block 44A or 44B (shown, e.g., in FIGS. 3 and 14). A pull wire 46 (not shown in FIGS. 4 and 5) may extend through the body 50 and spring 52 substantially along the axis B. The spring 52 may apply a distal force to the pin 54, such that the pin 54 pinches the pull wire 46 against the interior of the body 50 to maintain a stable connection between the pull wire 46 and the clip subassembly 48. Thus, as the clip subassembly 48 receives a proximal force from a slider block 44, the clip subassembly. 48 directly transfers the force to a pull wire 46 to deflect the shaft 18.

Figure 10:
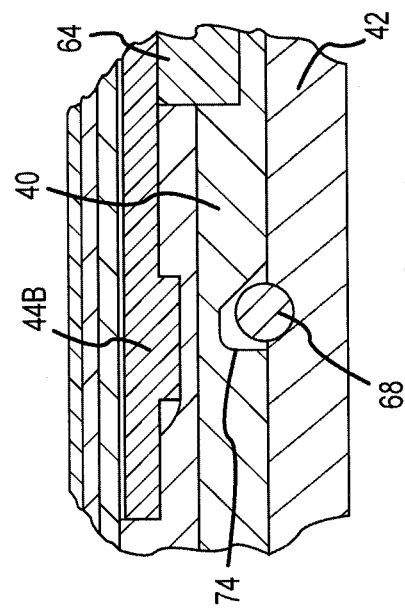
FIG. 10 is an enlarged view of a portion of FIG. 9.
Figure 9:
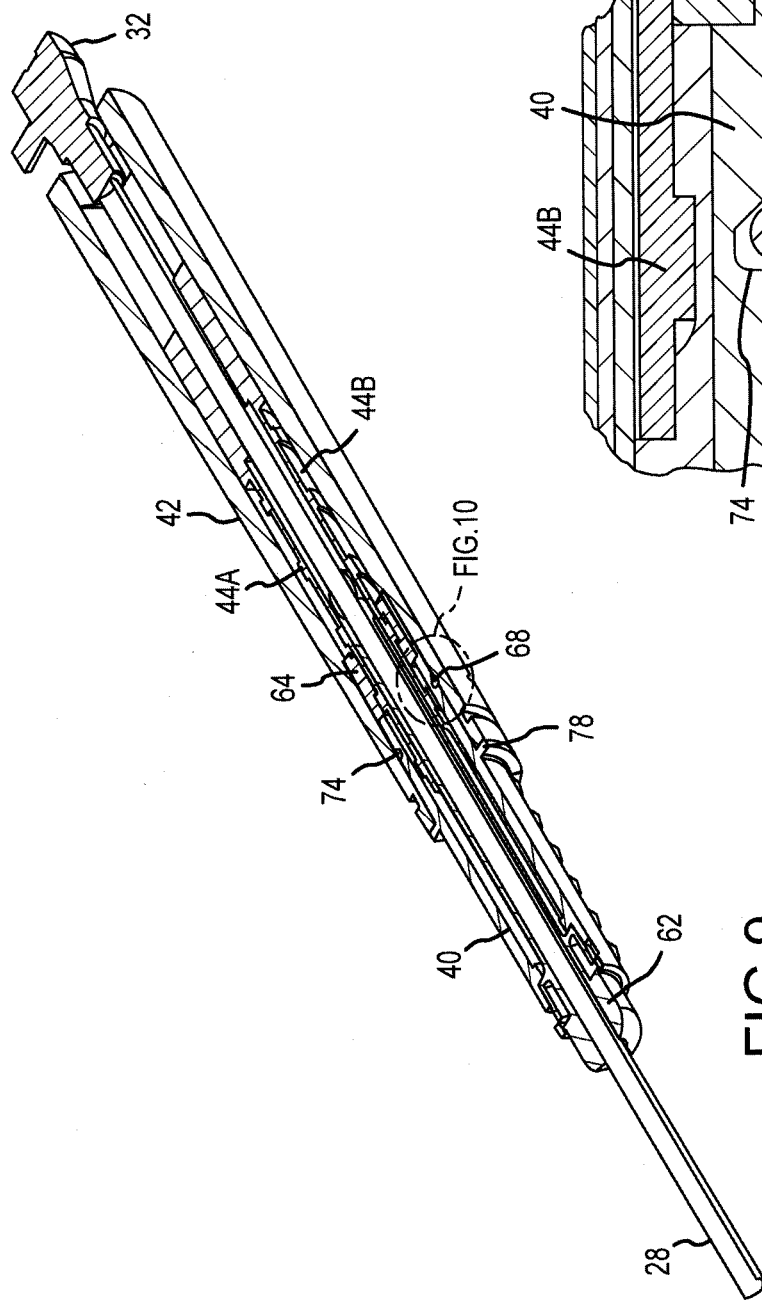
FIG. 9 is a cross-sectional view of the interior assembly illustrated in FIG. 6.

FIG. 6 is a exploded isometric view of an interior assembly 60 of an embodiment of the handle assembly 24 with the pull wires 46 and clip subassemblies 48A, 48B removed for clarity of illustration. FIG. 7 is a cross-sectional view of the interior assembly 60, also with the clip subassemblies 48A, 48B and the portion of the pull wires 46 that extend from the slider blocks 44A, 44B to the clip subassemblies 48A, 48B removed for clarity of illustration. FIG. 8 is an enlarged side view of an embodiment of a dowel pin. FIG. 9 is a cross-sectional view of the interior assembly 60, also with the clip subassemblies 48A, 48B and the pull wires 46 removed for clarity of illustration. FIG. 10 is an enlarged view of a portion of FIG. 9.

Referring to FIGS. 6-10, the interior assembly 60 may comprise a wire guide 62, the adjustment knob insert 40, a bushing 64, a first O-ring 66, a dowel pin 68, the mounting shaft 42, the slider blocks 44A, 44B, and a second O-ring 70. The interior assembly 60 may be generally disposed about an axis A. In an embodiment, the axis A may also be the central axis of the shaft 18 (see FIGS. 1 and 2).

With continued reference to FIGS. 6-10, the wire guide 62 may be disposed at the distal end of the interior assembly 60 and extend proximally through the insert 40, the bushing 64, and a portion of the mounting shaft 42. The wire guide 62 may be configured to receive a shaft (i.e., the shaft 18 shown in FIGS. 1-3) and may provide a passage for the pull wires 46 from the handle assembly 24 to the shaft 18. The wire guide 62 may also provide a passage for other components between the handle assembly 24 and the shaft 18 such as, for example only, electrical leads or wires, and one or more lumens for passing fluid and/or other medical devices, such as a catheter and/or guidewire, therethrough. The wire guide 62 may also comprise a coupling mechanism 72 for attachment with another component, such as the adjustment knob insert 40. The coupling mechanism 72 may be a snap-fit protrusion (as shown in FIGS. 6 and 7) or any other appropriate coupling mechanism known in the art.

The adjustment knob insert 40 and bushing 64 may be configured to transfer force (i.e., circumferential force) from an exterior mechanism (i.e., the adjustment knob 26, see FIGS. 1-3) to the slider blocks 44. The insert 40 may comprise a knob coupling portion 58 including one or more features for securing the insert to the adjustment knob such as, for example only, barbs or a knurled surface. The insert 40 may further comprise an annular circumferential groove 74 in its exterior surface for interacting with the dowel pin 68 to create an automatic locking, or "autolock" feature, as further explained below, and a circumferential protrusion 78 configured to abut the mounting shaft 42.

The dowel pin 68 may define a longitudinal axis C and include a chamfered surface 76 at one end and may have a circular cross-section, in an embodiment. In an embodiment, the angle $\theta_1$ of the chamfer may be configured in design and manufacture to interact with a chamfered surface of the groove 74 of the insert 40. The dowel pin 68 may additionally or alternatively include a rounded end surface, a flat end surface, a different cross-section, and/or another appropriate structural feature.

Figure 11:
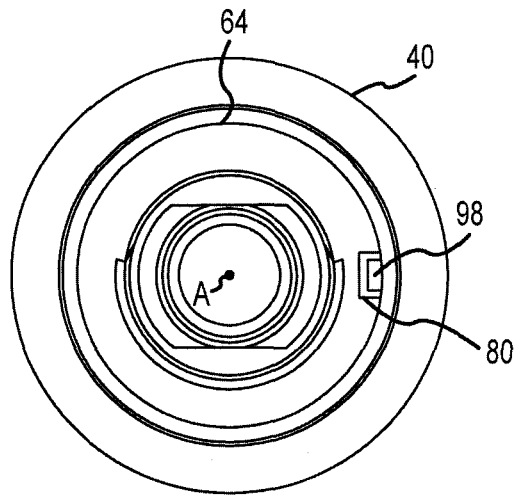
FIG. 11 is an end view of an embodiment of the bushing and adjustment knob insert of the interior assembly of FIG. 6.
Figure 12:
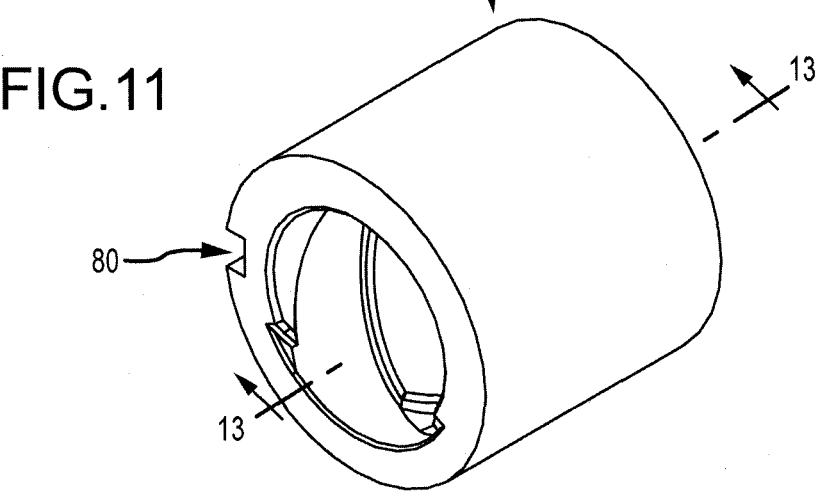
FIG. 12 is an enlarged isometric view of the bushing of FIGS. 6, 7, 9, and 10.
Figure 13:
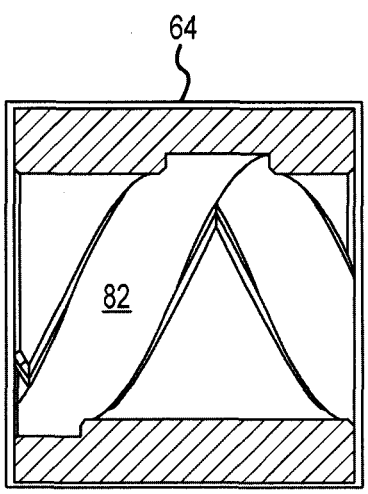
FIG. 13 is a cross-sectional view of the bushing of FIGS. 6, 7, 9, and 10.

The bushing 64 may be disposed inside the insert 40, and the bushing 64 and insert 40 may include complementary mechanical features so that the bushing 64 and insert 40 rotate in unison. For example, the insert 40 may have a longitudinal protrusion 98, and the bushing may have a longitudinal groove 80, as shown in greater detail in FIGS. 11 and 12, such that the insert 40 and the bushing 64 are fixed rotationally about the axis A.

Referring to FIGS. 6, 7, 9, 11-13, and 16, the bushing 64 may also include interior threads 82 for engaging threads 90 on the slider blocks 44. Because the insert 40 and the bushing 64 may rotate in unison, a rotation of the insert 40 may rotate the bushing 64, which may move the slider blocks 44 proximally and distally via interaction of complementary threads 82, 90 to increase and decrease tension in one or more pull wires. In an embodiment, the bushing 64 may comprise one or more metals, such as aluminum. The bushing 64 may additionally or alternatively comprise one or more plastics or polymers such as, for example only, polycarbonate, such as that available under the trade name Makrolon™ from Bayer MaterialScience. The bushing 64 may also comprise nylon and/or another plastic or polymer such as acrylonitrile butadiene styrene (ABS) or polyether imide (PEI). In a plastic or polymer embodiment, the bushing 64 may be manufactured according to a process involving injection molding, machining, and/or other processes known in the art. In an alternate embodiment, the bushing 64 may be omitted, and the interior threads 82 may be provided on an interior surface of the insert 40.

In an embodiment, the insert 40 may comprise one or more plastic materials. For example, the insert may comprise polycarbonate, such as that available under the trade name Makrolon™ from Bayer MaterialScience. The insert 40 may also comprise nylon and/or another plastic or polymer such as acrylonitrile butadiene styrene (ABS) or polyether imide (PEI). The insert 40 may be manufactured according to a process involving injection molding, machining, and/or other processes known in the art.

The mounting shaft 42 may house the slider blocks 44 and may receive the portion of the adjustment knob insert 40 that holds the bushing 64 and includes the circumferential groove 74. At the same longitudinal position as the circumferential groove 74, the mounting shaft 42 may include a pinhole 84 for receiving and securing the dowel pin 68. As mentioned above, the dowel pin 68 may interact with the circumferential groove 66 to create an autolock feature.

Figure 16:
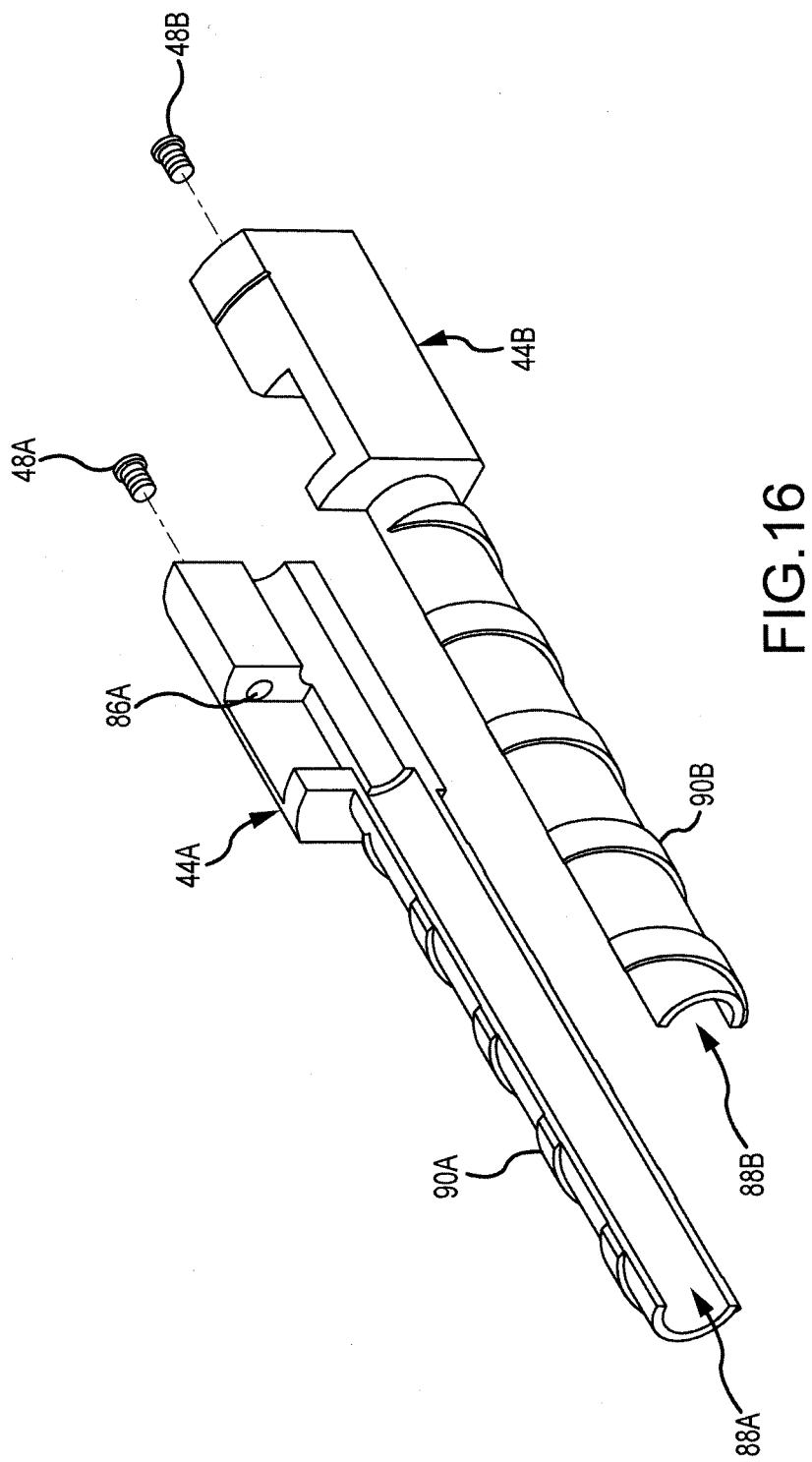
FIG. 16 is an isometric view of an embodiment of slider blocks that may be a part of the interior assembly of FIGS. 3, 6, 7, 9, and 10.

Referring to FIGS. 3, 6, and 16, the slider blocks 44 may be disposed inside of the mounting shaft 42 and may each comprise a pull wire hole 86, an interior channel 88, and exterior threads 90 configured to interact with the interior threads 82 of the bushing 64. Each slider block 44 may abut a clip subassembly 48 (see FIG. 3) such that movement of the slider block 44 directly applies or releases tension to/from a pull wire 46. Each pull wire 46 may extend distally through a respective pull wire hole 86 and channel 88, through the remainder of the handle assembly 24, and through the shaft 18 as described above. The slider block channels 88 may also allow longitudinal passage of electrical wiring, fluid lumens, and/or a guidewire that may be connected or inserted at the proximal end of the handle assembly 24 (see FIG. 2).

In an embodiment, the slider blocks 44A, 44B may have opposite threads (e.g., the first slider block 44A may have left-handed threads 90A, and the second slider block 44B right-handed threads 90B) so that the slider blocks 44A, 44B move in opposite directions when the bushing 64 rotates. Such opposite threading 90A, 90B may be provided for a device having opposing pull wires 46A, 46B where the first pull wire 46A deflects the shaft 18 in a first direction and the second pull wire 46B deflects the shaft 18 in a second direction that is different from the first. In an embodiment, the second direction may be about one hundred and eighty degrees (180°) offset from the first. Of course, in an embodiment, a different relative angle between the pull wires may be included. Furthermore, in an embodiment, only a single pull wire may be included, or more than two pull wires may be included.

Figure 14B:
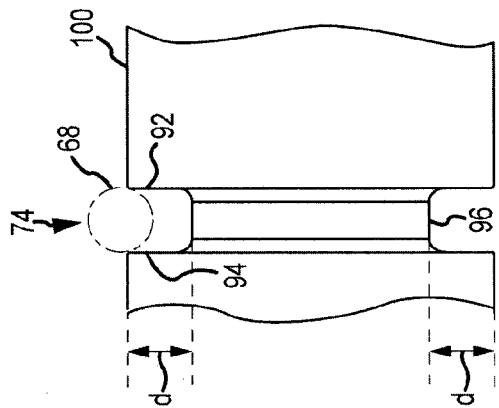
FIGS. 14A and 14B are side views of a first embodiment of an adjustment knob insert that may be a part of the interior assembly of FIGS. 3, 6, 7, 9, and 10.
Figure 14A:
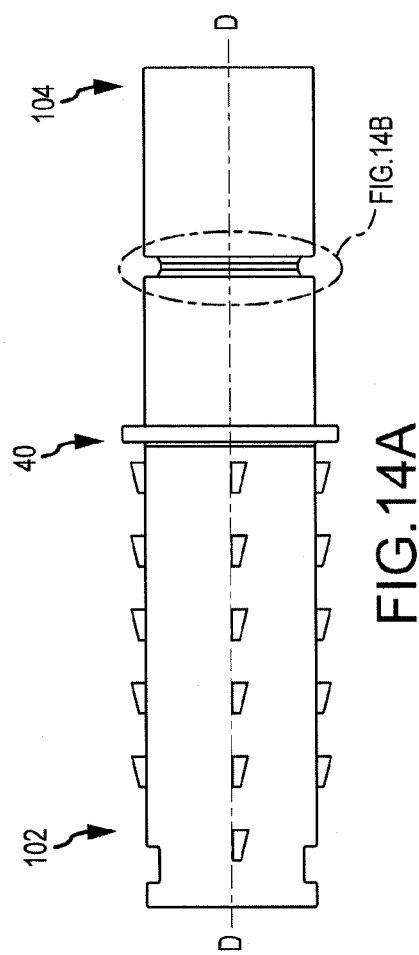

FIG. 14A is a side view of the adjustment knob insert 40 and FIG. 14B is an enlarged side view of a portion of the insert 40. The insert 40 may include, in addition to the features mentioned above, an annular groove 74 having a depth d, a first sidewall 92, a second sidewall 94, an interior surface 96, and may extend from a distal end portion 102 to a proximal end portion 104 along axis D about which the insert 40 may be configured to rotate. In an embodiment, the axis D may be coincident with or otherwise parallel to the axis of the interior assembly of which the insert 40 forms a part (i.e., axis A, see FIG. 6). Both the first sidewall 92 and the second sidewall 94 may be substantially perpendicular to a line that is parallel to the axis D, as well as to an exterior surface 100. The interior surface 96 may comprise a number of flat or curved segments forming a collectively concave interior surface, as shown, or may have another shape or configuration. The depth d may be chosen as appropriate based on the materials of the insert 40 and other factors. For example, if the insert 40 comprises plastic, polymer, or another deformable material, the depth d of the groove 74 may be relatively deeper (i.e., as compared to an insert made of or comprising a less deformable material, such as metal, such as aluminum). In an embodiment, the depth d of the groove 74 may be approximately 0.1 inches.

As noted above, the groove 74 is configured to interact with a dowel pin (i.e., dowel pin 68, see FIGS. 6 and 8-10) to create autolock. The dowel pin 68 and insert 40 may be configured so that a tip of the dowel pin 68 is disposed within the groove 74 with the dowel pin 68 extending generally transverse to the interior surface 96 of the groove 74, as shown in FIG. 14B. Further, when assembled, the axis C of the dowel pin (see FIG. 8) may be positioned within the groove 74. As the insert 40 rotates about the axis A, there may be friction between the dowel pin 68 and one or more of the first sidewall 92, the second sidewall 94, and the interior surface 96. With two perpendicular sidewalls 92, 94 as illustrated in FIGS. 14A and 14B, and plastic, polymer, or other relatively deformable material comprising the insert, there may be relatively little friction between the dowel pin 68 and the interior surface 96 of the groove 74. As a result, the majority of the force opposing rotation of the insert 40 may be imparted from the dowel pin 68 to a sidewall (i.e., the first sidewall 92) and may be substantially parallel to the axis of rotation D. Thus, the insert 40 shown in FIGS. 14A and 14B may be used to create a relatively weaker autolock as compared to the embodiment of FIGS. 15A-15B, discussed below.

Figure 15B:
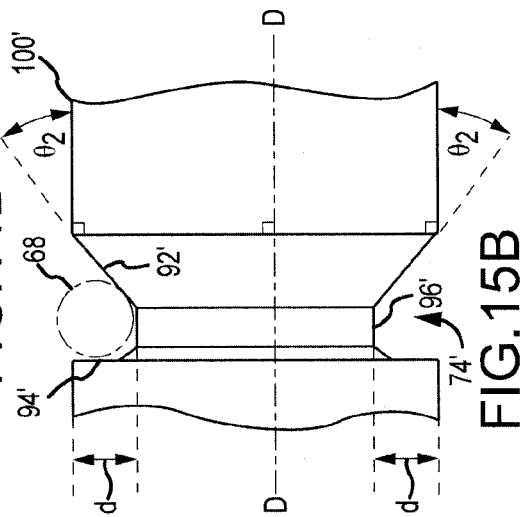
FIGS. 15A and 15B are side views of a second embodiment of an adjustment knob insert that may be a part of the interior assembly of FIGS. 3, 6, 7, 9, and 10.
Figure 15A:
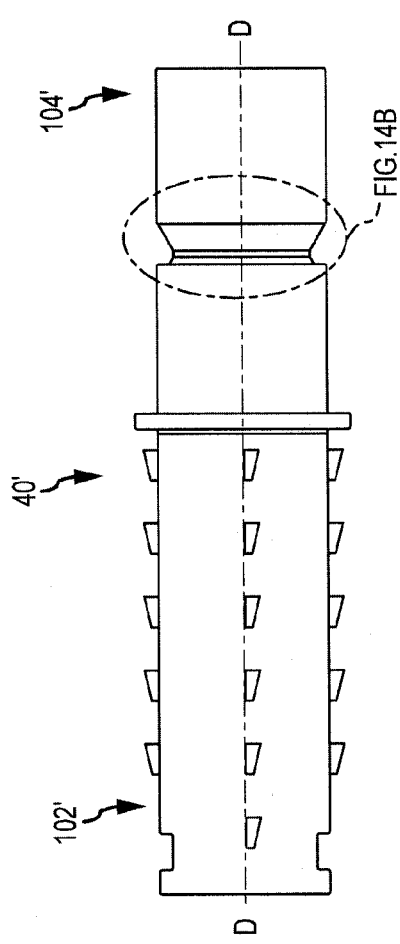

FIG. 15A is a side view of a second embodiment of an adjustment knob insert 40' and FIG. 15B is an enlarged side view of a portion of the insert 40', which may be similar to insert 40 described above. For example, the insert 40' may be identical to the insert 40 (see FIGS. 14A and 14B) except for the configuration of the groove 74'. In the second 40', the groove 74' includes a first sidewall 92' that includes a chamfer or is beveled with respect to the exterior surface 100', a second sidewall 94' that includes a portion that is perpendicular to a line parallel to the axis D, and an interior surface 96'.

The chamfer of sidewall 92' may extend at an angle $\theta_2$ relative to a line parallel to the axis D. The appropriate angle $\theta_2$ may be determined experimentally or through simulations for an appropriate amount of friction with a dowel pin (e.g., the dowel pin 68) to create an appropriate autolock strength. The appropriate angle $\theta_2$ for the chamfer may depend on the coefficient of friction of the respective materials used for the insert 40' and the dowel pin 68, the shape of the dowel pin 68, and the depth of the groove 74', for example only. In an embodiment, $\theta_2$ may be about forty-five (45) degrees.

The groove 74' may have a depth d that may be chosen as appropriate based on the materials of the insert 40' and other factors. For example, if the insert 40' comprises plastic, polymer, or another deformable material, the depth d of the groove 74' may be relatively deeper (i.e., as compared to an insert made of or comprising a less deformable material, such as metal, such as aluminum). In an embodiment, the depth d of the groove 74' may be approximately 0.1 inches.

Because of the chamfer in the first sidewall 92', force opposing rotation of the insert 40' as a result of friction between the dowel pin 68 and the groove 74' may include components that are both parallel to the axis D and perpendicular to the axis D. Additionally, the total force opposing rotation, i.e., the friction force components that are parallel to the axis D, may be greater than in the configuration of the first insert 40'. Accordingly, the second insert 40' may be used when a relatively stronger autolock is desired (i.e., with more force required to rotate the adjustment knob 26 and deflect the shaft 18, see FIG. 2).

Figure 17A:
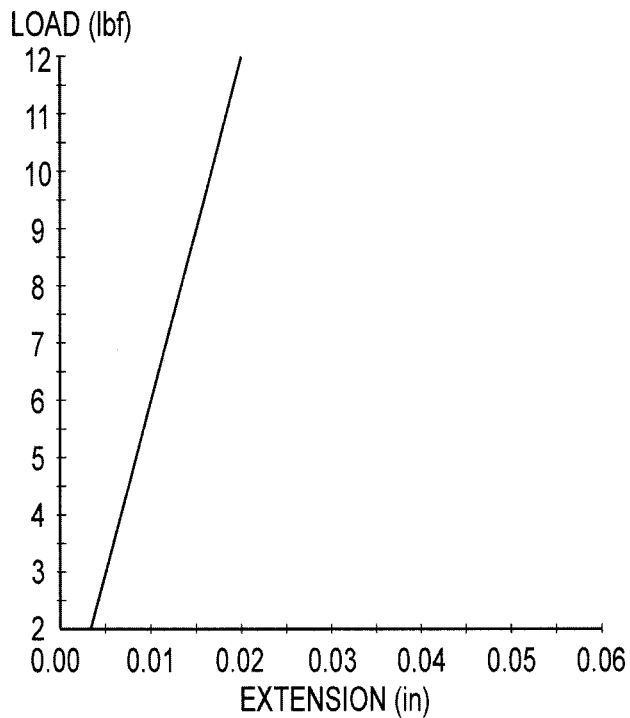
FIG. 17A is a plot illustrating the load capacity of an exemplary interior assembly including the first adjustment knob insert embodiment shown in FIGS. 14A and 14B.
Figure 17B:
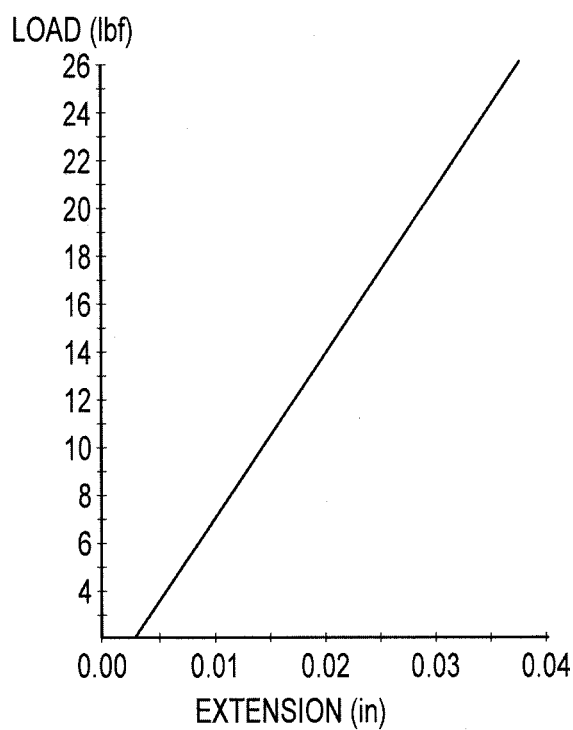
FIG. 17B is a plot illustrating the load capacity of an exemplary interior assembly including the second adjustment knob insert embodiment shown in FIGS. 15A and 15B.

FIGS. 17A and 17B are plots illustrating the relative amounts of autolock force that embodiments of the inserts 40, 40' may enable, respectively. For example, an in embodiment, as noted above, the inserts 40, 40' may comprise a plastic material. In such an embodiment, the insert 40 may enable autolock force as shown in FIG. 17A. As shown in FIG. 17A, a plastic embodiment of the insert 40 may enable up to about 12 lbf at an extension of a slider block 44A, 44B of about 0.02 inches. Further slider block extension, however, may cause the force between the dowel pin 68 and the groove 74 to become so great that the groove 74 may deform and the dowel pin slip from the groove 74, disabling the autolock feature.

In contrast, and as shown in FIG. 17B, the chamfer in the first sidewall 92' allows the insert 40' to enable up to about 26 lbf at an extension of a slider block 44A, 44B of about 0.04 inches. Thus, as demonstrated by FIGS. 17A and 17B, the addition of a chamfer to the first sidewall 92' improves both the total force of the autolock feature and the effective movement range of the autolock feature over a non-chamfered embodiment.

Both the first and second inserts 40, 40' may comprise a plastic or polymer material, as noted above. As a result, the inserts 40, 40' may be relatively less expensive to manufacture than a similar metal component and may additionally be lighter. Accordingly, plastic or polymer inserts of one of the configurations illustrated in FIGS. 14A-15B may be preferred over metal inserts.

Although a number of embodiments have been described above with a certain degree of particularity, those skilled in the art could make numerous alterations to the disclosed embodiments without departing from the spirit or scope of this disclosure. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A handle assembly for an elongate medical device, comprising:
    an exterior adjusting knob extending along a longitudinal axis and configured to rotate about said axis;
    an insert configured to engage said adjusting knob and to rotate about said axis responsive to rotation of said adjusting knob, said insert comprising an annular groove configured to engage a dowel pin, said annular groove comprising a sidewall comprising a chamfer; and
    a dowel pin configured to engage said annular groove to resist rotation of said insert;
    wherein said insert is configured to rotate about said axis to actuate one or more pull wires to deflect a shaft of the elongate medical device.

2. The handle assembly of claim 1, wherein said insert further comprises first threads configured to be coupled to a slider having complementary second threads, the slider coupled to a pull wire and configured to apply a tensile force to the pull wire responsive to rotation of said adjusting knob.

3. The handle assembly of claim 2, wherein said insert further comprises a bushing, said bushing comprising said first threads.

4. The handle assembly of claim 1, wherein said insert comprises a polymer or plastic.

5. The handle assembly of claim 1, wherein said insert comprises a distal end portion and a proximal end portion, wherein said sidewall comprises a first sidewall, said annular groove further comprising a second sidewall, wherein said first sidewall is closer to said proximal end portion than said second sidewall is to said proximal end portion.

6. The handle assembly of claim 1, wherein said insert further comprises a plurality of barbs configured to engage said adjusting knob.

7. The handle assembly of claim 1, wherein said annular groove has a transverse depth of approximately 0.1 inches or more.

8. The handle assembly of claim 1, wherein said chamfer of said sidewall extends at an angle of approximately 45 degrees relative to a line parallel to said axis.

9. The handle assembly of claim 1, wherein said adjusting knob is disposed about at least a portion of said insert.

10. A handle assembly for an elongate medical device, comprising:
    an exterior adjusting knob extending along a longitudinal axis and configured to rotate about said axis;
    a polymer or plastic insert configured to engage said adjusting knob and to rotate about said axis responsive to rotation of said adjusting knob, said insert comprising an annular groove configured to engage a dowel pin; and
    a dowel pin configured to engage said annular groove to resist rotation of said insert when no external force is applied to said adjusting knob, wherein said insert is configured to rotate relative to said dowel pin when an external force is applied to said adjusting knob.

11. The handle assembly of claim 10, wherein said annular groove comprises a sidewall comprising a chamfer.

12. The handle assembly of claim 1, wherein said sidewall is a first sidewall, said annular groove further comprising a second sidewall extending substantially perpendicular to a line parallel to said axis.

13. The handle assembly of claim 12, wherein said chamfer extends at an angle of approximately 45 degrees relative to a line perpendicular to said axis.

14. The handle assembly of claim 12, wherein said annular groove has a transverse depth of approximately 0.1 inches or more.

15. The handle assembly of claim 12, wherein said insert further comprises a plurality of barbs configured to engage said adjusting knob.

16. The handle assembly of claim 12, wherein said annular groove further comprises a concave interior radial surface.

17. An elongate medical device comprising:
    a shaft comprising a distal end portion, a proximal end portion, a longitudinal axis extending through said distal and proximal end portions, and a pull wire coupled to said distal end portion configured to deflect said distal end portion; and
    a handle assembly coupled to said proximal end portion, said handle assembly comprising:
        an exterior adjusting knob extending along said axis and configured to rotate about said axis;
        an insert configured to engage said adjusting knob and to rotate about said axis responsive to rotation of said adjusting knob, said insert comprising an annular groove configured to engage a dowel pin, said annular groove comprising a beveled sidewall, wherein rotation of said insert applies a tensile force to said pull wire to deflect said shaft distal end portion; and
        a dowel pin configured to engage said annular groove to maintain the longitudinal position of said insert and to resist rotation of said insert;
    wherein said shaft and said handle assembly are configured to allow another medical device to be passed therethrough.

18. The elongate medical device of claim 17, wherein said insert comprises a polymer or plastic material.

19. The elongate medical device of claim 17, wherein said handle assembly further comprises an exterior grip portion disposed about at least a portion of said insert.

* * * * *